United States Patent [19]

Duncan

[11] Patent Number: 5,103,822
[45] Date of Patent: Apr. 14, 1992

[54] PACING SYSTEM FOR TERMINATION OF CARDIAC ARRHYTHMIAS UTILIZING SCANNING TECHNIQUES

[75] Inventor: James L. Duncan, Alpharetta, Ga.

[73] Assignee: Siemens-Pacesetter, Inc., Sylmar, Calif.

[21] Appl. No.: 504,501

[22] Filed: Apr. 3, 1990

[51] Int. Cl.⁵ ............................................. A61N 1/362
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,942,534 | 3/1976 | Allen et al. | 128/419 PG |
| 3,949,758 | 4/1976 | Jirak | 128/419 PG |
| 4,312,356 | 1/1982 | Sowton et al. | 128/419 PG |
| 4,390,021 | 6/1983 | Spurrell et al. | 128/419 PG |
| 4,398,536 | 8/1983 | Nappholz et al. | 128/419 PG |
| 4,406,287 | 9/1983 | Nappholz et al. | 128/419 PG |
| 4,408,606 | 10/1983 | Spurrell et al. | 128/419 PG |
| 4,427,011 | 1/1984 | Spurrell et al. | 128/419 PG |
| 4,541,430 | 9/1985 | Elmqvist et al. | 128/419 PG |
| 4,561,442 | 12/1985 | Vollmann et al. | 128/419 PG |
| 4,574,437 | 3/1986 | Segerstad et al. | 128/419 PG |
| 4,577,633 | 3/1986 | Berkovits et al. | 128/419 PG |
| 4,726,380 | 2/1988 | Vollmann et al. | 128/419 PG |

Primary Examiner—Kyle L. Howell
Assistant Examiner—Kennedy J. Schaetzle
Attorney, Agent, or Firm—Bryant R. Gold; Malcolm J. Romano; Lisa P. Weinberg

[57] ABSTRACT

A system and method for terminating a cardiac arrhythmia includes pacing means for stimulating the heart with at least one stimulation pulse during a narrow region of susceptibility (termination window) of the arrhythmia cycle. The location of the region of susceptibility is initially found by delivering the stimulation pulse(s) to the heart in accordance with a prescribed scan pattern. The scan pattern delivers the stimulation pulse(s) at a time during the cardiac cycle such that each successive stimulation pulse is presented to the heart at a slightly different time than was a prior stimulation pulse, thereby assuring that the region of susceptibility or termination window is eventually located. When the arrhythmia is successfully terminated, the location of the successful stimulation pulse within the prescribed scan pattern is stored. Upon the next occurrence of a cardiac arrhythmia, the initial stimulation pulse is presented to the heart at a time within the prescribed scan pattern that is backed up from the location of the prior successful stimulation pulse by a prescribed amount. Thus, even though the region of susceptibility may have moved in either direction within the cardiac cycle, the initial stimulation pulse of the next scanning sequence is likely to be applied at a location within the cardiac cycle that is near and moving towards the region of susceptibility.

32 Claims, 3 Drawing Sheets

PACING SYSTEM FOR TERMINATION OF CARDIAC ARRHYTHMIAS UTILIZING SCANNING TECHNIQUES

BACKGROUND OF THE INVENTION

The present invention relates to cardiac pacemakers, and more particularly to an implantable cardiac pacemaker having means for detecting and terminating a cardiac arrhythmia, such as a tachycardia. Even more particularly, the present invention relates to applying a scanning stimulation pulse to the heart during each cardiac cycle in accordance with a prescribed sequence, i.e., a sequence wherein the timing of the stimulation pulse relative to the cardiac cycle varies slightly from one occurrence to the next. Through this process, the time region between successive heart beats is scanned for the purpose of finding a time where the stimulation pulse terminates the cardiac arrhythmia. Once the cardiac arrhythmia is terminated, and upon the next occurrence of a cardiac arrhythmia, the scanning stimulation pulse is applied to the heart beginning at a location in its prescribed sequence that is backed up a prescribed amount from the previous location in the prescribed sequence where the stimulation pulse successfully terminated the prior cardiac arrhythmia.

Cardiac pacing, i.e., the selective application of a simulation pulse to the heart, has been utilized for many years for the purpose of terminating intrinsic atrial and/or ventricular arrhythmias. A tachycardia is an arrhythmia in which the heart beats very rapidly, e.g., above 150 beats per minute. The principle underlying cardiac pacing for the purpose of terminating a tachycardia is that if a pacemaker stimulates the heart at least once shortly after a heartbeat, before the next naturally occurring heart beat at the rapid rate, the heart may revert to sinus or natural rhythm. This is because a tachycardia is often the result of electrical or other feedback within the heart. That is, a natural heartbeat results in the feedback of an electrical or other stimulus which may prematurely trigger another beat. By injecting a stimulation pulse within the cardiac cycle, the stability of the feedback loop is disrupted, and the heart may revert to a sinus (natural) rhythm.

The difficulty in using a stimulation pulse to terminate a tachycardia lies in determining exactly when the stimulation pulse should be applied. It must be applied shortly after a heartbeat and prior to the time when the next premature beat would otherwise occur. Said another way, it must be applied at a certain time within the cardiac cycle. As the cardiac cycle is manifest by, e.g., the occurrence of R-waves (with each R-wave representing the depolarization of ventricular muscle tissue), the stimulation pulse must therefore be applied at a time between successive R-waves. However, there is usually only a short period of time, hereafter termed the "region of susceptibility", somewhere between successive beats (R-waves) during which the generation and application of a stimulation pulse has a high probability of successfully terminating a tachycardia. Unfortunately, this region of susceptibility varies not only from patient to patient, but from day to day with the same patient. Moreover, for any given patient on any given day, the "region of susceptibility" within the overall tachycardia cycle is relatively short, and may vary even during a single tachycardia episode. (Note, as used herein, the term "region of susceptibility" refers to that narrow time period within a given arrhythmic cycle during which the heart is susceptible to reverting back to a sinus rhythm through the application of a stimulation pulse. This time period may be thought of as an arrhythmia termination window. The terms "region of susceptibility" and "termination window" are used interchangeably herein to refer to this narrow time period.)

In order to increase the likelihood that a stimulation pulse will be applied during the region of susceptibility, and therefore be successful in terminating a tachycardia, or other arrhythmia, it is known in the art to use several techniques to hunt for and find the region of susceptibility. Typically, heretofore, the manner in which the "hunting" for the region of susceptibility has been accomplished follows one of two approaches: (1) "shotgunning" the region between successive R-waves with a burst of pulses; or (2) scanning successive single or multiple stimulation pulses through a scanning window.

Shotgunning is premised on the theory that by providing a burst of pulses, the likelihood that at least one of the pulses will fall within the region of susceptibility of the heart significantly increases. If not, the rate of the pulses within the burst (i.e., the time spacing of pulses within the burst), or the position of the burst relative to the cardiac cycle, is modified slightly and reapplied to the heart during a subsequent heart cycle. This process continues until the region of susceptibility is found, and the tachycardia terminates. Once found, the timing associated with the successful burst may be stored and used as the starting point for applying a new burst of simulation pulses to the heart upon the next occurrence of a tachycardia. U.S. Pat. Nos. 4,398,536 (Nappholz et al.); 4,406,287 (Nappholz et al.); 4,408,606 (Spurrell et al.); 4,541,430 (Elmqvist et al.); and 4,561,442 (Vollmann et al.) are representative of this shotgun (burst pacing) approach of terminating a tachycardia.

The other way to find the region of susceptibility is to define a scanning window, e.g., a period of time between successive heart beats, through which one, two or more successive stimulation pulses are applied in a controlled sequence. The controlled sequence may be, e.g., beginning at one end of the scanning window and scanning in a controlled manner towards the other end of the window with each successive stimulation pulse or group of pulses. Hence, the stimulation pulse scans through the scanning window looking for the region of susceptibility. For example, as taught in U.S. Pat. No. 4,312,356, issued to Sowton et al., a pacer is provided wherein the sensing of a tachycardia triggers a stimulation pulse having a known, and somewhat arbitrary timing, relative to the tachycardia cycle. This stimulation pulse is thus applied to the heart at a time within the cardiac cycle that represents a first guess of the location of the region of susceptibility. If the stimulation pulse is not successful in terminating the tachycardia, i.e., if the first guess is incorrect, then a subsequent stimulation pulse is provided so as to be issued later or earlier relative to the timing of the unsuccessful stimulation pulse. In this trial-and-error manner, the region of susceptibility is eventually located, and the tachycardia is terminated. Unfortunately, this approach may require a significant "hunting" time before the region of susceptibility is located.

In order to shorten the hunting time, it is also known in the art to store the timing associated with the last successful stimulation pulse(s). This timing is then used as a starting point when the next tachycardia occurs. In this manner, the "hunting" time is believed to be significantly reduced. U.S. Pat. Nos. 4,390,021 (Spurrell et al.) and 4,427,011 (Spurrell et al.) are representative of the prior art approaches taken using a pulse that hunts for the region of susceptibility by scanning through a scanning window. U.S. Pat. No. 4,577,633 (Berkovits et al.) accomplishes essentially the same result (of providing a single scanning stimulation pulse that hunts for the region of susceptibility) by continuously shortening the pacemaker escape interval with each subsequent beat, for a predetermined number of beats, by a small programmable decrement.

It is also known in the art to combine shotgunning (burst pacing) and single-pulse scanning as selectable options within a single pacemaker, as is taught, e.g., in U.S. Pat. No. 4,726,380 (Vollmann et al.).

Burst pacing has been very successful in terminating cardiac arrhythmias, and was initially the preferred approach. However, experience has shown that its continued use may result in a significant incidence of arrhythmia acceleration, and a corresponding worsening of the hemodynamic state of the heart. (As used here, "hemodynamic" refers to the ability of the heart to efficiently perform its function as a pump.) As a result, the stimulation pulse scanning techniques have been favored in an attempt to lessen the risk of arrhythmia acceleration while maintaining a high efficacy for arrhythmia termination. Scanning of the stimulation pulse has been necessary in order to account for the variations in the exact timing of the "region of susceptibility" (or tachycardia termination window) that regularly occurs in any given patient. For example, changing blood levels of antiarrhythmic drugs, postural changes, catecholamine levels, and numerous other factors which affect the conduction velocity and refractory characteristics of cardiac tissue, may result in a movement of the region of susceptibility for any given patient.

Scanning may involve the use of one, two, or three pulses, or a burst of pulses. Typically, after each pacing attempt which is unsuccessful in terminating the arrhythmia, one or multiple of the cycle lengths of the pulses are reduced, and the new critically timed intervals are thereafter used. If this attempt is unsuccessful, the reduction is continued. In this way, the pulses are delivered sooner and sooner within the cardiac cycle, and the time between pulses (if multiple pulses are used) becomes shorter and shorter. Depending on the total range of cycle lengths to be reduced, the amount of reduction within each attempt, and the number of pulses and sequence to be reduced, an entire cycle of scanning may be a long process. Hence, it is known in the art, as mentioned, to use the memory of the device to automatically restart any new scanning sequence at the intervals which were last successful for termination. Unfortunately, however, if the region of susceptibility (termination window) has shifted in a direction that causes longer intervals for termination, this starting point of the scanning sequence may require an entire scan to be completed before finding the termination window. What is needed, therefore, is an arrhythmia termination system that prevents long periods of time in hunting for the region of susceptibility.

SUMMARY OF THE INVENTION

In accordance with one aspect of the invention, a cardiac arrhythmia is terminated by stimulating the heart with one or multiple stimulation pulses during the narrow region of susceptibility (termination window) of the arrhythmia cycle. The location of the region of susceptibility is found by delivering a stimulation pulse or a group of pulses to the heart during each cardiac cycle at a time during the cardiac cycle that is defined by a prescribed scan pattern. In accordance with the prescribed scan pattern, each successive stimulation pulse, or group of pulses, is presented to the heart at a slightly different time than was a prior stimulation pulse or group of pulses, thereby assuring that the region of susceptibility or termination window is eventually located. If the arrhythmia is successfully terminated, then the location of the successful stimulation pulse, or group of pulses, within the prescribed scan pattern is stored. Upon the next occurrence of a cardiac arrhythmia, the initial stimulation sequence is presented to the heart at a time within the prescribed scan pattern that is backed up from the location of the prior successful stimulation pulse, or group of pulses, by a prescribed amount. In this manner, the likelihood of quickly locating the region of susceptibility is significantly increased because the possibility of just missing this region with the initial stimulation pulse of the next sequence, as might occur where the region has moved within the cardiac cycle away from the location where it was last found, is all but eliminated. Thus, the possibility of having to pass through the entire scan pattern in order to again locate the termination window is also all but eliminated. That is, regardless of the direction in which the region of susceptibility (termination window) may have moved, the initial stimulation pulse of the next scanning sequence will advantageously be applied at a location within the cardiac cycle that is either coincident with, or near and moving towards (in accordance with the prescribed scan pattern), the new location of the region of susceptibility. Hence, the region of susceptibility may be advantageously located very quickly for cardiac arrhythmias occurring subsequent to the initial arrhythmia.

In accordance with another aspect of the invention, a method for terminating a cardiac arrhythmia through the select application of one or more stimulation pulses within the cardiac cycle is provided by: (a) detecting a cardiac arrhythmia; (b) presenting at least one stimulation pulse to the heart at an initial location within the cardiac cycle; (c) presenting a subsequent stimulation pulse or pulses at a different location within the cardiac cycle in the event the arrhythmia is not terminated, this different location being defined by a prescribed scan pattern, the prescribed scan pattern providing for the eventual application of stimulation pulses to substantially all regions of interest within the cardiac cycle; (d) repeating step (c) until the cardiac arrhythmia terminates; (e) storing the location within the prescribed scan pattern of the stimulation pulse that successfully terminates the cardiac arrhythmia; (f) in the event of a subsequent cardiac arrhythmia, issuing a new stimulation pulse or pulses at an initial location within the cardiac cycle corresponding to the location within the scan pattern of a stimulation pulse occurring prior to the location in the prescribed scan pattern of the stimulation pulse that successfully terminated the prior cardiac arrhythmia; and (g) issuing subsequent stimulation pulses, as required, at different locations within the cardiac cycle as defined by the prescribed scan pattern, commencing with the initial location of the new stimulation pulse, until the cardiac arrhythmia terminates.

Advantageously, the cardiac arrhythmia termination system and method of the present invention may be included in an implantable medical device, such as a pacemaker. The medical device, e.g., pacemaker, may operate in a conventional pacemaker mode, providing stimulation pulses to the heart of a patient on demand in order to maintain a desired cardiac rhythm, and step in with the arrhythmia termination method herein described only when a cardiac arrhythmia is detected.

It is thus a feature of the present invention to provide a system and method for use with an implantable pacemaker that quickly terminates a detected cardiac arrhythmia, such as a tachycardia.

It is yet another feature of the invention to provide an arrhythmia termination system and method that, subsequent to the occurrence of an initial arrhythmia, applies a stimulation pulse to the heart during a given cardiac cycle near or coincident with the narrow termination window (region of susceptibility) of the heart.

It is still another feature of the invention to provide such a cardiac arrhythmia termination system and method that minimizes the hunt time for the termination window (region of susceptibility) for any arrhythmia occurring after the termination of an initial arrhythmia, regardless of whether a single, multiple, or a burst of stimulation pulses are used. In particular, it is a feature of the invention to always begin the "hunt" for the termination window of any cardiac arrhythmia subsequent to the initial arrhythmia at a location within the cardiac cycle that is either coincident with, or near and moving towards, the likely location of the termination window.

It is a further feature of the invention to provide such a system and method for terminating cardiac arrhythmias that accounts for the possibility that the termination window (region of susceptibility) may move in either direction between successive arrhythmias.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
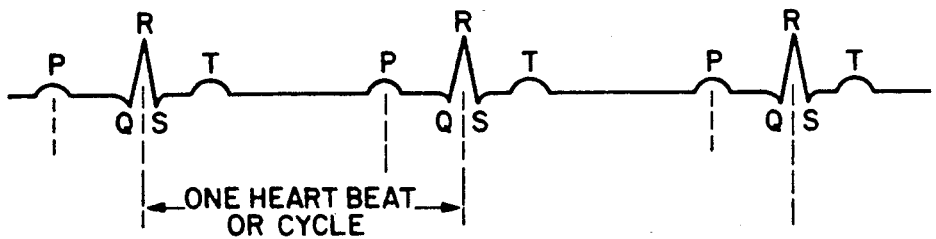
FIG. 1 depicts a typical ECG-type waveform illustrating normal sinus rhythm of the heart.

Referring to FIG. 1, there is shown a typical ECG-type waveform illustrating the normal operation and cardiac cycle of a heart. Such waveforms may be obtained using conventional skin-electrode ECG techniques. Alternatively, intracardiac ECG features of modern pacemakers may provide similar ECG information through the use of the telemetry features of such pacemakers. Beginning at the left of the waveform there is shown a P-wave. This P-wave represents the electrical activity coincident with the depolarization of the atria of the heart. Depolarization of the atria is accompanied by contraction of the atria, thereby allowing blood to be pushed from the atria into the ventricles of the heart. While those skilled in the art will recognize that depolarization and contraction are not necessarily simultaneous events, they will be assumed to be simultaneous events for purposes of this patent application, and the terms "depolarization" and/or "contraction" are meant to be synonymous.

A short time subsequent to the generation of the P-wave, the QRS complex appears, representing the depolarization of the ventricles. The time period between the P-wave and the QRS wave (often referred to as simply an R-wave) is a very important time interval in the operation of the heart because it represents the time needed for the blood to flow from the atria into the ventricles. The R-wave is followed by a T-wave, which represents the electrical activity associated with the repolarization of the ventricles. As known to those skilled in the art, the ventricles do most of the work in pumping the blood throughout the body. Typically, one heart beat or heart cycle is measured as the time interval between succeeding R-waves, simply because the R-wave typically represents the easiest of the waves to identify and measure. A heart beat could, of course, be measured relative to any point within the heart cycle, such as between succeeding T-waves or P-waves.

The important point to recognize is that a certain rhythm or synchrony occurs when the heart is functioning efficiently. That is, the depolarization of the atria, represented by the P-wave, is followed a short time thereafter by the depolarization of the ventricles, represented by the R-wave. After a sufficient delay, the atria again depolarize, followed by the depolarization of the ventricles. If the depolarization of the atria or ventricles do not occur naturally, then a pacemaker may be employed to provide stimulation pulses to these respective heart chambers, in order to trigger the required depolarization/ contraction at the appropriate time periods of the heart cycle.

Figure 2:
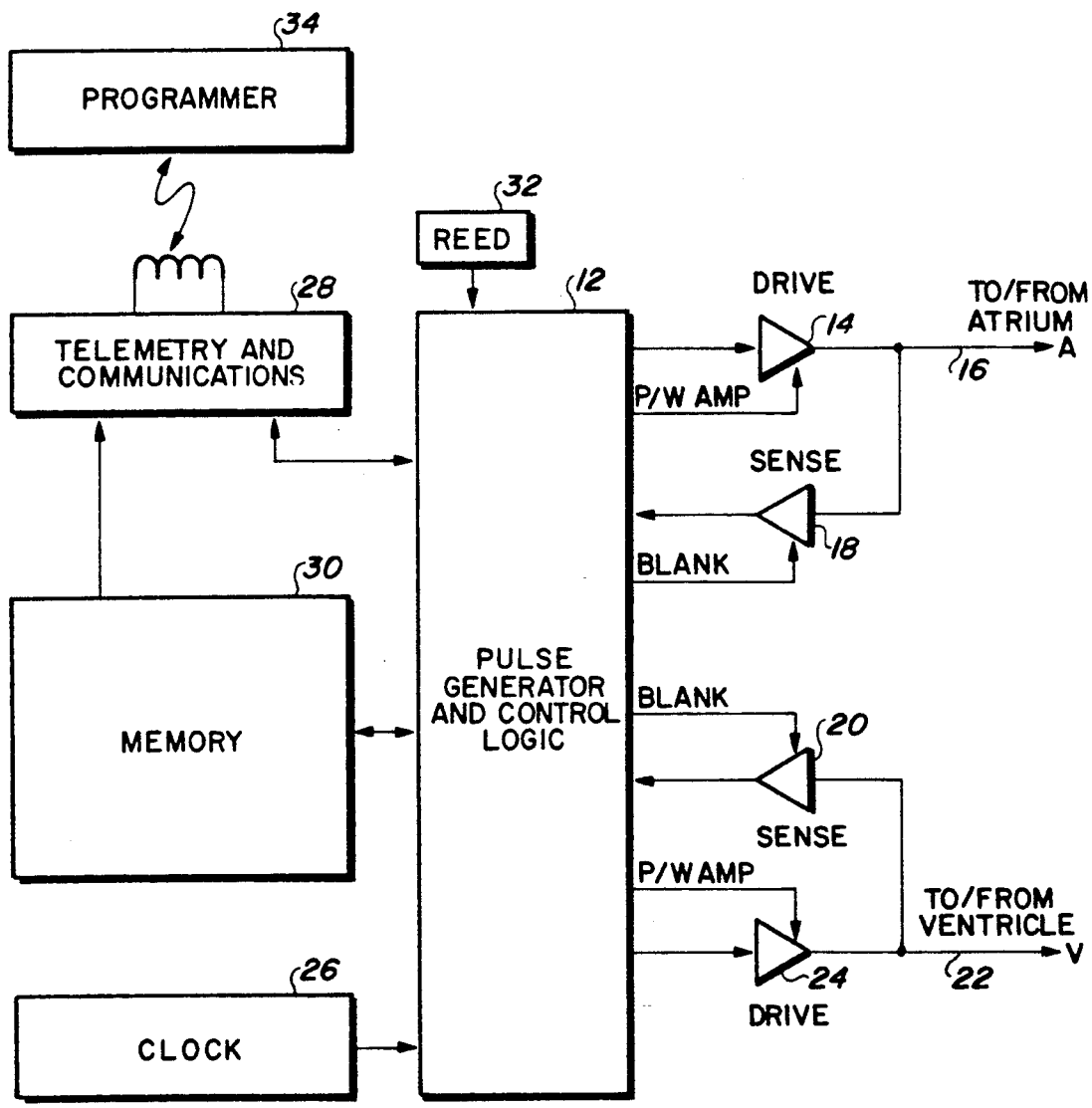
FIG. 2 is a block diagram of an implantable, programmable, dual-chamber pacemaker.

Referring next to FIG. 2, a block diagram of a typical atrial tracking dual-chamber pacemaker is illustrated. Pulse Generator and Control Logic 12 generates the appropriate timing sequences and stimulation pulses for delivery to the heart. Stimulation pulses are delivered to the right atrium of a heart (not shown) through an atrial drive amplifier 14 and an atrial lead or conductor 16. This same atrial lead 16 is connected to an atrial sense amplifier 18. This sense amplifier 18 monitors the electrical activity of the atrium to determine if a sinus P-wave, representing the natural depolarization of the atrium, has occurred. If such sinus atrial activity is sensed, then the Pulse Generator 12 inhibits the stimulation pulse provided to the drive amplifier 14 and provides for a tracked ventricular stimulus after a predetermined time period (referred to as the sensed AV delay). However, if after a prescribed period of time, typically referred to as the atrial escape interval, a sinus P-wave has not been sensed, then the Pulse Generator 12 delivers a stimulation pulse, through the drive amplifier 14, to the atrium over lead 16. The pulse width and amplitude of this stimulation pulse are controlled by the Pulse Generator and Control Logic 12.

In a similar manner, the Pulse Generator and Control Logic 12 senses the electrical activity occurring in the right ventricle of the heart through a sense amplifier 20 connected to a ventricular lead 22. If naturally occurring ventricular electrical activity is not sensed within an appropriate ventricular escape interval, then the Pulse Generator and Control Logic 12 generates a ventricular stimulation pulse of a prescribed pulse width and amplitude, delivered through the drive amplifier 24, in order to cause the desired ventricular contraction.

Clock circuitry 26 provides the basic clock signal from which the pulse generator and control logic 12 operates. Telemetry and communications circuitry provides a means whereby information can be telemetered to and from the implanted pacemaker. Control information that varies the basic escape intervals of the pacemaker, for example, may be received through the telemetry and communications circuitry 28 and stored in a memory 30, as may control information that sets the desired pulse width and/or amplitude of the stimulating pulse. Such control information may also be passed directly to the Pulse Generator and Control Logic 12, if desired. Similarly, electrical activity of the heart, as sensed through the sense amplifiers 18 and 20, can be telemetered external to the pacemaker through the telemetry and communications circuitry 28, thereby allowing an attending physician or other medical personnel, e.g., cardiologist, to monitor the activity of the heart without the use of external skin electrodes. A magnetic reed switch 32 is also typically employed with implanted pacemakers in order to control the programmable functions of the device. With a suitable programming apparatus in place, the attending physician or cardiologist can effectuate any desired changes in the operation of the pacemaker by sending appropriate control signals and commands over the telemetry and communications circuitry 28.

Figure 3:
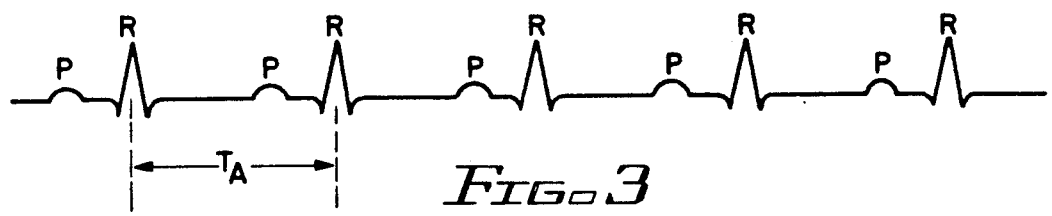
FIG. 3 is a timing diagram of an ECG-type waveform illustrating tachycardia wherein the heart beats at a rapid rate.

Referring next to FIG. 3, a timing diagram of an ECG-type waveform illustrating one type of cardiac arrhythmia (tachycardia) is shown. For simplicity, only the R-waves and P-waves are shown (i.e., the T-waves are omitted). This waveform appears similar to the normal cardiac rhythm shown in FIG. 1 except that the time duration between successive R-waves is much shorter, i.e., the cardiac cycle or period $T_A$ is much shorter in FIG. 3 than it is in FIG. 1. This means that the heart rate for the arrhythmia shown in FIG. 3 is much faster than is the normal heart rate shown in FIG. 1. This is, of course, the nature of a tachycardia—a rapid rhythm of the heart. In the discussion that follows, it will be assumed that a tachycardia is the particular cardiac arrhythmia that exists and that needs to be terminated. In some forms of arrhythmias, for example, the tachycardia may be a ventricular tachycardia, manifest by the occurrence of R-waves at a rapid rate, with only an occasional P-wave. In other forms, both R-waves and P-waves may occur each cycle.

Figure 4A:
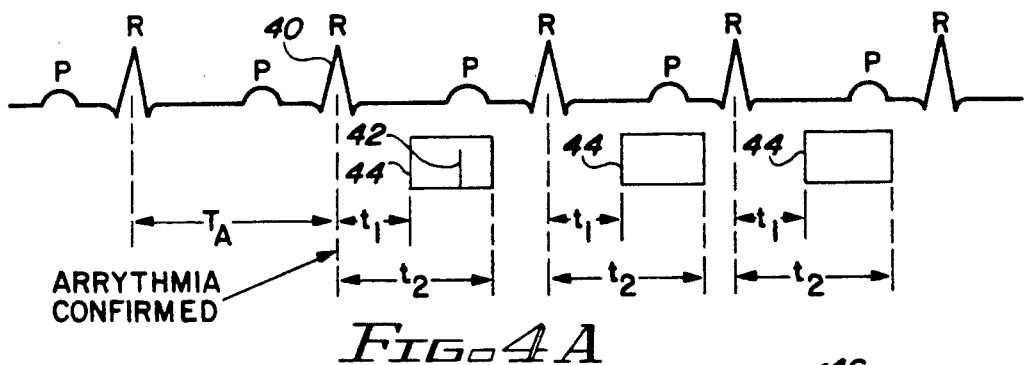
FIG. 4A is a composite timing diagram illustrating a tachycardia as in FIG. 3, and further illustrating the use of a scanning window during which a stimulation pulse is applied to the heart in an attempt to terminate the arrhythmia.

The manner of addressing a cardiac arrhythmia, e.g., a tachycardia, in accordance with the present invention is illustrated in FIG. 4A. As shown in FIG. 4A, and as a first step in practicing the invention, the occurrence of a cardiac arrhythmia, such as a tachycardia, must be detected. Conventional means for detecting such an arrhythmia may be employed, such as are commonly used in an implantable pacemaker. Typically, such means involve monitoring the time interval between successive R-waves (or other recurring events in the cardiac cycle waveform) to determine if such interval is too short for a normal rhythm under the existing conditions. This determination is usually made over several cardiac cycles in order to avoid having a single short cycle of the heart trigger a tachycardia termination mode when in fact no tachycardia has occurred. In other words, some means are typically employed to ensure that a sustained tachycardia exists before efforts are undertaken to terminate the tachycardia.

In FIG. 4A, it is assumed that the particular arrhythmia is confirmed at the occurrence of R-wave 40. This confirmation triggers an arrhythmia termination mode. Such mode causes a stimulation pulse 42 to be generated at a particular time within a scanning window 44. The scanning window is generated during each cardiac cycle and has a fixed, although programmable, relationship relative to a predetermined recurring event in the cardiac cycle, such as the occurrence of an R-wave. Hence, as shown in FIG. 4A, the scanning window begins at time delay $t_1$ after the occurrence of R-wave 40, and ends at time delay $t_2$ after the occurrence of R-wave 40. The size of the scanning window 44 (i.e., its relative length compared to the cardiac cycle or period $T_A$) is selected so as to likely include the narrow region of susceptibility of the heart.

The stimulation pulse 42 assumes a location within the scanning window as defined by a predetermined scan pattern. The scan pattern causes the stimulation pulse 42 to scan through the scanning window 44 over several cardiac cycles, with one stimulation pulse being generated in each scanning window, but at a different location in the scanning pattern. However, the scanning pattern is selected to ensure that all regions of interest in the scanning window eventually receive a stimulation pulse if the termination mode is still enabled.

While only a single stimulation pulse 42 is shown in FIG. 4A, it is to be understood that multiple stimulation pulses may also be applied, with a first pulse of, e.g., a group of multiple pulses, being represented by the stimulation pulse 42. That is, in the discussion that follows, it is to be understood that or the stimulation pulse 42 need not necessarily be a single stimulation pulse, but rather may represent a group or bundle of pulses, or a burst of pulses. A single pulse is shown for clarity for explanation, not for purposes of limiting the invention.

Those skilled in the art will appreciate that it is not necessary in defining the scanning window 44 to specify both the time delay $t_1$ and the time delay $t_2$. Rather, one can be defined, and the other can be inferred from the particular scan pattern that is used.

Figure 4B:
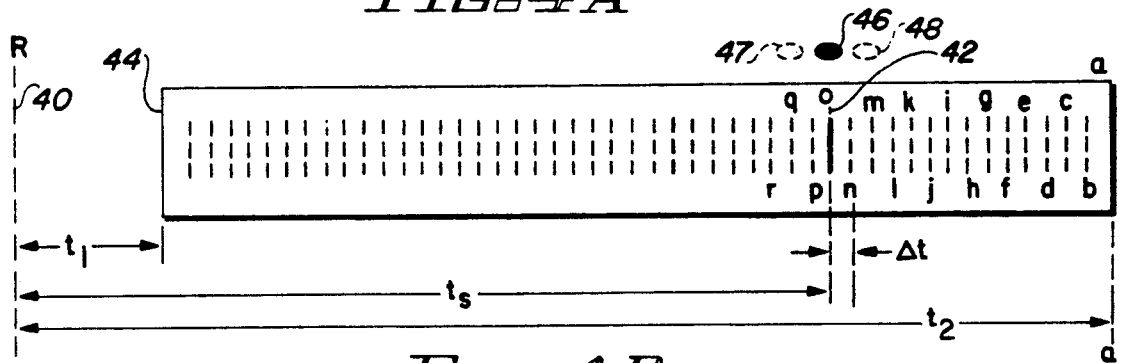
FIG. 4B is an expanded diagram of the scanning window of FIG. 4A, and illustrates the manner in which the stimulation pulse(s) is/are generated so as to assume one of a plurality of possible locations within the scanning window in accordance with a prescribed scanning sequence.

FIG. 4B is an expanded diagram of the scanning window 44 of FIG. 4A, and illustrates one manner in which the stimulation pulse 42 is generated so as to assume one of a plurality of possible locations within the scanning window in accordance with the prescribed scanning sequence or scan pattern. In FIG. 4B, a plurality of possible locations, a, b, c, d, . . . , for the stimulation pulse 42 within the scan window 44 are identified. These possible locations are preferably equally spaced a distance $\Delta t$ apart from each other. The particular scan pattern that is used causes the stimulation pulse 42 to assume a first location within the scan pattern, such as location "a", during the first scan window after confirmation of the arrhythmia. During the second scan window, the stimulation pulse assumes a second location, such as location "b". This process continues with the stimulation pulse moving around within the scanning window 44 each time scanning window is generated for so long as the termination mode continues. This is done in order to locate or hunt for the narrow region of susceptibility of the heart. If the region of susceptibility of the heart is located, the termination mode is discontinued. However, the location of the stimulation pulse (or group of pulses) within the scanning window that successfully terminated the arrhythmia, i.e., the location of thee region of susceptibility relative to the scanning window, is stored. Upon the next occurrence of a tachycardia or other arrhythmia, i.e., upon entry into the termination mode a second time, the first stimulation pulse (or group of pulses) is applied to the heart at a location relative to the scanning window that is backed up a prescribed amount from the previously stored location of the prior successful stimulation pulse. The scan pattern then continues forward from that new starting point. In this manner, if the region of susceptibility has moved relative to the scanning window during the time span between the first arrhythmia and a second arrhythmia, not an uncommon occurrence, the next sequence of stimulation pulses will be applied to the heart beginning at a location within the scanning window that is likely near, and moving towards (in accordance with the scan pattern), the region susceptibility.

The above process will be explained further by way of an example presented in conjunction with FIG. 4B. Assume that the region of susceptibility is a narrow period of time represented by the darkened area 46. A scan pattern is selected that essentially moves the stimulation pulse(s) right to left through the scanning window 44. Thus, upon the confirmation of an arrhythmia, the first stimulation pulse is applied at a time corresponding to the location "a" of the scanning window 44, i.e., at the extreme right side of the scanning window (at time $t_2$ after the arrhythmia confirming R-wave 40). This stimulation pulse misses the region of susceptibility 46. Hence, the termination mode continues, and a second stimulation pulse is applied to the heart during the next cardiac cycle at location "b" (at time $t_2-\Delta t$ from the last R-wave). This second stimulation pulse also fails to hit the region of susceptibility 46, so a third stimulation pulse is applied at location "c" during the next cycle. This process continues until the region of susceptibility 46 is found by the stimulation pulse applied at location "o" of the scan pattern, which stimulation pulse causes the arrhythmia to terminate, thereby causing the termination mode to end. The initial scan pattern may thus be described, using the letter identifiers of the possible locations within the scanning window 44 where a stimulation pulse may be applied, as the sequence:

a b c d e f g h i j k l m n o (terminates).

Thus, in this example, the 15th stimulation pulse of this initial scan pattern successfully terminates the arrhythmia.

Continuing with this example, upon the successful termination of the arrhythmia, the location "o" of the scanning pattern is saved or stored. At a subsequent time, a second arrhythmia is confirmed, causing the termination mode to be enabled. In accordance with the present invention, the first stimulation pulse to be applied, or the first group of stimulation pulses to be applied, begins at a location in the scan pattern that is backed up a prescribed amount from the prior stored location. If the prescribed back up amount is, e.g., three positions, the new stimulation pulses are applied, beginning at location "1", and proceeding right to left. Thus, if the region of susceptibility had moved to a new location, such as location 47 (to the left of the prior location 46), the stimulation pulse sequence is:

l m n o p q (terminates).

Hence, termination occurs at the sixth pulse of the sequence. However, and even more significantly, if the region of susceptibility had moved to a new location 48 that is right of the prior location 46, the simulation pulse sequence is just:

l m (terminates).

Thus, in this example, termination occurs at the second pulse of the sequence. Had the sequence not been backed up, but started at the stored location of the prior successful termination pulse, as is taught in the prior art, the termination sequence needed to find the region of susceptibility at location 48 would have to be:

o p q r . . . a b c d e f g h i j k l m (terminates).

In other words, the stimulation pulse would have to scan through the entire scanning window, and begin again through the window on a second scan, before the region of susceptibility could be found. This would not only take a significant amount of time, but would also result in the expenditure of significant amounts of energy in the stimulation pulses that "missed" the region of susceptibility. In contrast, in accordance with the present invention, by backing up the starting location of the next sequence of pulses, it is likely that the region of susceptibility will be located in a very short time.

Advantageously, the amount of back up is a programmable variable that may be selected by a physician to suit the needs of a particular patient. Some patients may exhibit relatively small movement of the region of susceptibility, in which case the amount of back up can be programmed to a small value (two or three steps), while other patients may exhibit large movement, in which case the amount of back up can be programmed accordingly (10-15 steps). The same is true for a single patient at different times. E.g., if the patient is administered drugs that may cause increased movement of the region of susceptibility, the doctor can reprogram the termination mode for that patient to include a larger back up amount.

Further, the particular scan pattern that is utilized by the termination mode of the present invention may also be programmed to a desired sequence. (Programming of selected parameters may occur in a conventional manner as known in the art and as taught in connection with FIG. 2.) A simple right-to-left scan pattern was described in the example presented above. However, it would also be just as simple to use a left-to-right scan pattern. Moreover, a two-steps-forward, one-step-backward, scan pattern could be employed. Such a scan pattern would, using the predefined locations shown in FIG. 4B, follow the sequence:

a c b d c e d f e g f h ...

Other scan patterns could also be defined, limited only by the skill and imagination of the programming physician and the needs of a particular patient.

Figure 5:
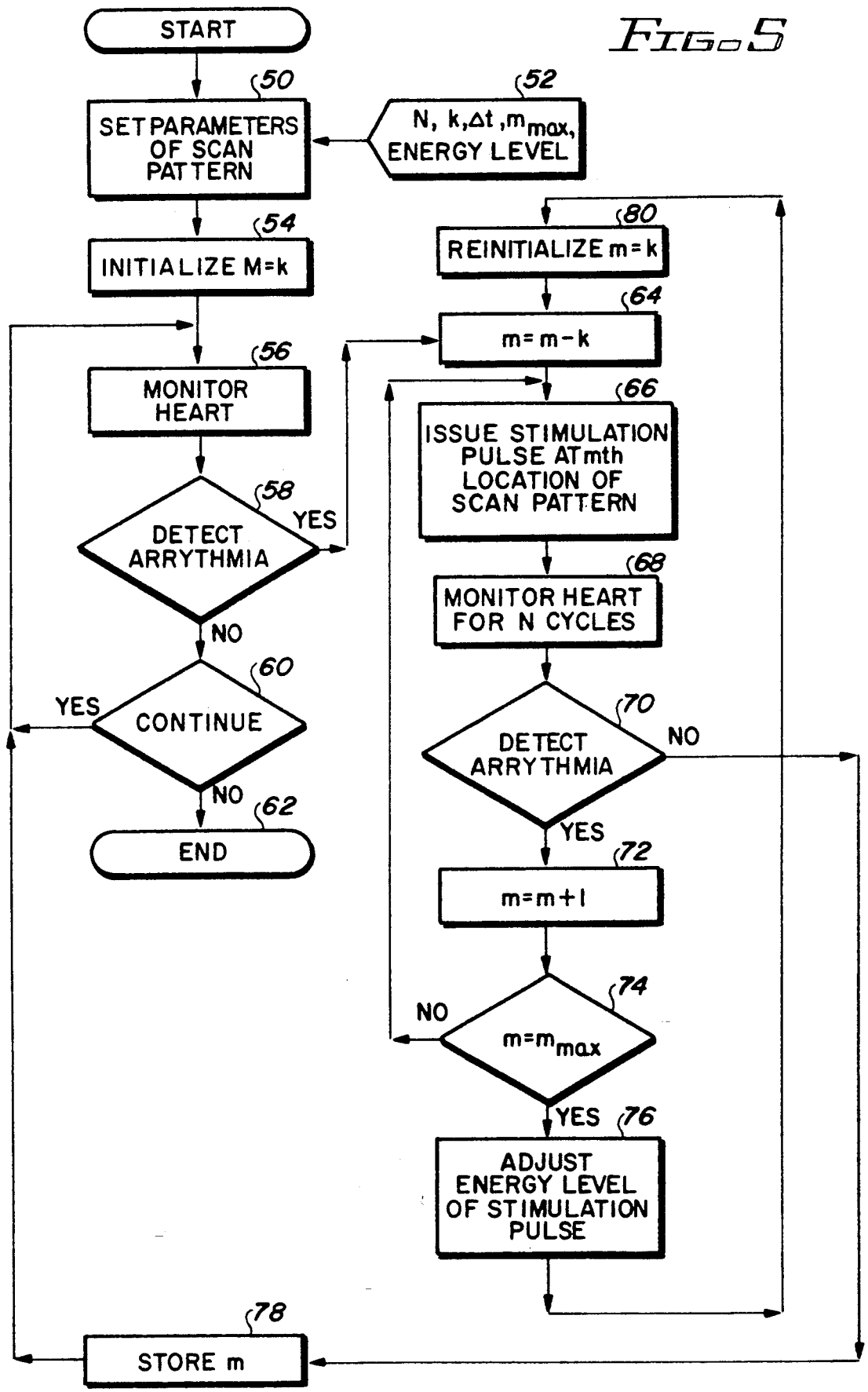
FIG. 5 is a flow chart of a preferred method for terminating a cardiac arrhythmia in accordance with the present invention.

Referring next to FIG. 5, a simplified flow chart of a preferred method for terminating a cardiac arrhythmia in accordance with the present invention is depicted. This method may be carried out in a programmable medical device that includes means for generating and delivering a stimulation pulse, or a group of stimulation pulses at a desired time within the cardiac cycle, and means for detecting a cardiac arrhythmia. Such means are included in most programmable implantable cardiac pacemakers. Hence, the present invention may be carried out using such pacemakers that have been modified to carry out the method shown in FIG. 5.

The flow chart of FIG. 5 will now be explained in more detail by making reference to the block numbers identified in the flow chart, where each "block" describes some step of decision that is made as the method is carried out. Before the method is used, certain initialization steps must be taken, as indicated in block 50. Primarily, these steps include setting the parameters that define the scan pattern. Such parameters, as indicated in block 52, include, e.g.: N, the number of cardiac cycles that are monitored to determine whether the arrhythmia has been successfully terminated; k, the amount of back up of the scan pattern, measured in scan pattern steps or increments; $\Delta t$, the amount of spacing between steps of the scan pattern; $m_{max}$, the maximum number of steps that are to be included in the scan pattern; and the energy level of the stimulation pulse(s).

Once the scan pattern is set, the system is initialized at block 54 by setting a tracking variable m equal to the programmed amount of back up, k. The tracking variable m tracks the location of the stimulation pulse within the scanning window. That is, when m is equal to zero, the stimulation pulse is applied to the first location in the sequence, e.g., location "a" in FIG. 4B. When m is equal to one, the stimulation pulse is applied to the second location in the sequence, and so on, such that when m is equal to n, where n is any integer, the stimulation pulse is applied to the nth location in the sequence.

After being initialized, the heart is monitored (block 56) to determine if an arrhythmia is present. If an arrhythmia is detected and confirmed (block 58), then the termination mode begins. If an arrhythmia is not detected, and if the method is to continue (block 60), then the heart continues to be monitored (block 56). If a physician wishes to disable the method, e.g., for the purpose of reprogramming the parameters or to perform other tests on the patient, a suitable exit command can be generated (through conventional programming means) to allow the method to terminate (blocks 60, 62).

When the termination mode begins, the value of the tracking parameter is set to its initial value at block 64 by making $m=m-k$. The first time an arrhythmia is detected, this value will be zero (at m was set equal to k at block 54). A stimulation pulse, or a group of stimulation pulses, is next issued (block 66) at the mth location of the scan pattern. For the first pulse of the first arrhythmia, this will be location 0 of the scan pattern, or the first location of the scan pattern (e.g., location "a" of FIG. 4B). After the stimulation pulse is issued, the heart is monitored for N cycles (block 68) in order to determine if the arrhythmia was terminated. If the arrhythmia continues, as confirmed at block 70, then m is incremented (block 72) to the next value of the sequence or scan pattern. A determination is next made as to whether the entire scan pattern has been completed (block 74). If not, control returns to block 66 where a new stimulation pulse is generated at the mth (now increased from the prior value) location of the scan pattern. If the entire scan pattern has been completed (block 74), i.e., if $m=m_{max}$, then the energy level of the stimulation pulse may be adjusted (block 76) and the scan pattern is commenced again by re-initializing m to the value of k (block 80). Such energy adjustment may be accomplished by increasing either the amplitude or pulse width of the stimulation pulse, or both.

It is to be noted that adjusting the energy of the stimulation pulse or pulses (block 76) and restarting the scan pattern (block 80) in response to completing an entire scan without successfully terminating the arrhythmia (block 74) is only one example of a remedial action that may be taken if the region of susceptibility is not located during the first pass through the scanning window. Other actions that could also be taken, either alone or in combination with adjusting the stimulation energy, include adjusting the scan pattern so that, e.g., $\Delta t$ is narrower. Or, an entirely different scan pattern could be invoked. Alternatively, no action could be taken other than to commence a second pass through the scan window using the same scan parameters as were used during the first pass. It is also possible to adjust the location of the scan window, as defined by the times $t_1$ and $t_2$ within the cardiac cycle. Indeed, the present invention contemplates that numerous options can be taken in order to suit the needs of a particular patient at a particular time.

If, as determined and confirmed at block 70, the arrhythmia is successfully terminated with a particular stimulation pulse or pulse group that was issued at the mth location of the scan pattern, then that value of m is stored (block 78). After storing, control jumps back to block 56 where the heart is monitored. If a subsequent arrhythmia is detected (block 58), then the value of m is decreased (block 64) by the back up amount, k, and a stimulation pulse or pulse group is issued (block 66) at this new (backed up) location m. The scan pattern then continues from that point forward.

Figure 6:
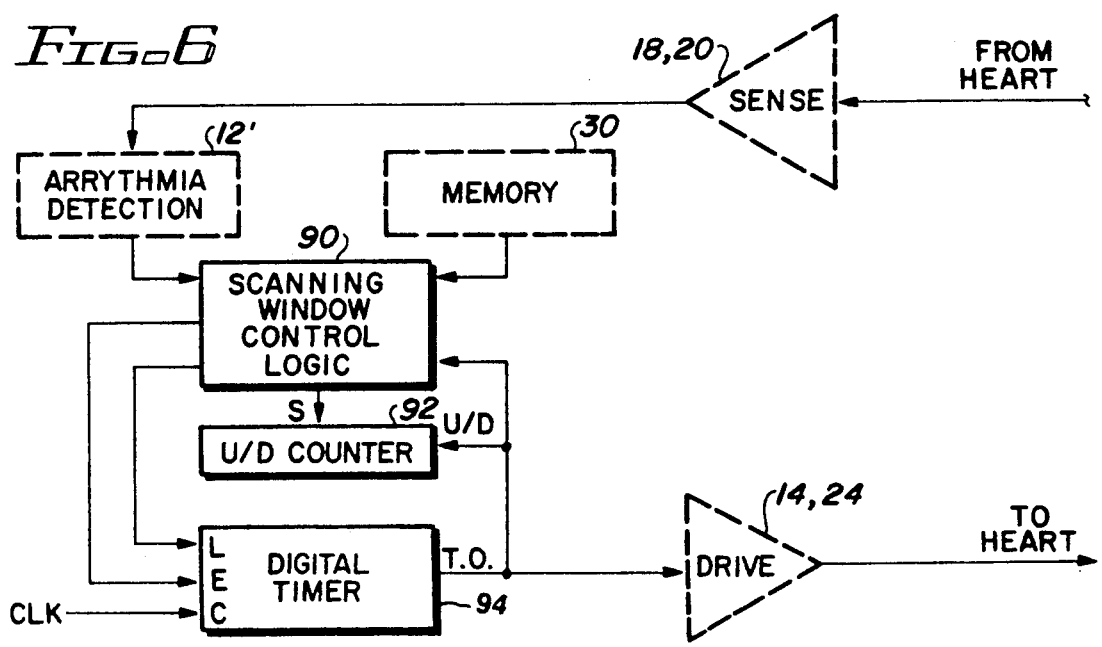
FIG. 6 is a block diagram of termination circuitry that may be used with the pacemaker of FIG. 2 in order to terminate a cardiac arrhythmia in accordance with the present invention.

Referring next to FIG. 6, a simplified block diagram of one embodiment of termination circuitry that may be used with the pacemaker of FIG. 2 in order to terminate a cardiac arrhythmia in accordance with the present invention is illustrated. In FIG. 6, those elements shown in dashed lines may be the same as corresponding elements of the implantable pacemaker described above in connection with FIG. 2. Arrhythmia detection circuitry 12' may be the same circuitry that is typically included in the pulse generator and control logic 12 of a conventional pacemaker. Upon confirmation of an arrhythmia by the arrhythmia detection circuitry 12', scanning window control logic 90 is enabled. This logic 90 generates an enabling pulse that is directed to the enablinq input, E, of a digital timer circuit 94, driven by a suitable clock signal. The logic 90 also loads an up-/down counter 92 with an appropriate starting count for the digital timer 94, which starting count is transferred to the timer 94 upon generation of a suitable load command, L. The starting count may be a value that is previously stored in memory 30, and may represent, e.g., the time delay value $t_2$ When the time 94 times out, it issues a time out (T.O.) signal that is coupled to the drive amplifiers 14 or 24 of the pacemaker, causing a stimulation pulse or pulses to be delivered to the heart. The T.O. signal is also fed back to the control logic 90 and the up/down counter 92. The up/down counter 92 responds to the T.O. pulse by, e.g., decrementing its count by one count. The control logic 90 responds to the T.O. pulse by disabling the timer 94 until the appropriate time within the cardiac cycle, e.g., until the occurrence of an R-wave within a confirmed arrhythmia. At the appropriate time within the cardiac cycle, the control logic 90 further issues a new load command, L, to the timer 94, causing the revised (decremented) count signal to be loaded into the timer. Thus, when the timer is again enabled, if it is enabled (and it will only be enabled at the occurrence of an R-wave if the arrhythmia detection circuit 12' confirms the arrhythmia is still present), another T.O. pulse will be issued at a time thereafter determined by the decremented count signal provided by the up/down counter 92. For a simple scan pattern, this time will be an amount Δt less than the previous time.

If an arrhythmia is terminated, the control logic 90 makes note of this fact and saves the value held in the up/down counter 92. At an appropriate time, this stored value can be "backed up" a desired amount so that upon the next confirmed occurrence of an arrhythmia, the digital timer will be loaded with the backed up value of the desired time delay.

It is submitted that those skilled in the art can readily fashion logic circuitry using conventional components to perform the functions of the control logic 90, up/down counter 92, and digital timer 94 as described above. In fact, both the digital timer and up/down counter circuits may be realized using off-the-shelf commercially available components. Further, the control logic 90 may be readily fashioned using conventional logic gates, latches, and similar elements. Ideally, all of the circuitry shown in FIG. 6, as well as the pacemaker circuitry shown in FIG. 2, is realized using custom or semi-custom LSI circuits that& are reduced to a small number of integrated circuit chips that can readily fit within an implantable medical device. Further, as is known in the art, the pulse generator and control logic 12 (FIG. 2) may include a microprocessor, which microprocessor may be programmed to provide any desired parameter values or automatic adjustment of parameter values.

As thus described, it is seen that the present invention provides a system and method for use with an implantable pacemaker that quickly terminates a detected cardiac arrhythmia, such as a tachycardia. Further, such system and method minimizes the use of potentially wasteful bursts of stimulation pulses. That is, the disclosed method avoids "shotgunning" the heart in an attempt to randomly "hit" the narrow termination window (region of susceptibility) of the heart with a stimulation pulse. Rather, the stimulation pulses are carefully and rapidly guided to the region of susceptibility. Moreover, the present invention provides such a cardiac arrhythmia termination system and method that significantly minimizes the hunt time for the termination window (region of susceptibility) for any arrhythmia occurring after the termination of an initial arrhythmia. Advantageously, the "hunt" for the region of susceptibility (subsequent to the occurrence of an initial arrhythmia) always begins at a location within the cardiac cycle that is either coincident with, or near and moving towards, the likely location of the region of susceptibility. This approach thus accounts for the possibility that the region of susceptibility may move in either direction between successive arrhythmias.

While the invention herein disclosed has been described by means of specific embodiments and applications thereof, numerous modifications and variations could be made thereto by those skilled in the art without departing from the scope of the invention set forth in the claims. For example, instead of using digital circuits for generating the scan pattern of the stimulation pulse within the scanning window, analog equivalents of such digital circuits could also be employed. Moreover, while the preferred embodiment of the invention is to be used in combination with an implantable pacemaker, the invention could also be employed by itself as, e.g., a diagnostic arrhythmia termination system, using either implantable or external cardiac pacing and sensing apparatus.

What is claimed is:

1. A method for terminating a cardiac arrhythmia by selectively applying a stimulation pulse within the cardiac cycle associated with said arrhythmia comprising:
   (a) detecting a cardiac arrhythmia;
   (b) presenting at least one stimulation pulse to the heart at an initial location within the cardiac cycle;
   (c) presenting at least one subsequent stimulation pulse at a different location within the cardiac cycle in the event the arrhythmia is not terminated, this different location being defined by a prescribed scan pattern that sets discrete incremental locations within said cardiac cycle whereat stimulation pulses may be applied, the prescribed scan pattern providing for the eventual application of stimulation pulses to substantially all regions of interest within the cardiac cycle over successive cardiac cycles;
   (d) repeating step (c) until the cardiac arrhythmia terminates;
   (e) storing the location within the prescribed scan pattern of the at least one stimulation pulse that successfully terminates the cardiac arrhythmia;
   (f) in the event of a subsequent cardiac arrhythmia, presenting at least one new stimulation pulse at an initial location within the cardiac cycle corresponding to a location within the prescribed scan pattern that is relocated a prescribed discrete increment from the location of the at least one stimulation pulse in the prescribed scan pattern that successfully terminated the prior cardiac arrhythmia; and
   (g) issuing subsequent stimulation pulses, as required, at different locations within the cardiac cycle as defined by the prescribed scan pattern, commencing with the initial location of the at least one new stimulation pulse, until the subsequent cardiac arrhythmia terminates.

2. The method set forth in claim 1 wherein step (b) comprises presenting the at least one stimulation pulse to the heart at the end of a first time delay after the occurrence of a detectable cardiac event within said cardiac cycle.

3. The method set forth in claim 2 wherein step (c) comprises presenting said at least one subsequent stimulation pulse to the heart at the end of a second time delay after the occurrence of a detectable and repeatable cardiac event within a subsequent cardiac cycle, such as an R-wave, said second time delay comprising said first time delay less a fixed increment, and wherein said prescribed scan pattern defines an mth time delay after which an mth stimulation pulse is provided as being equal to an (m−1)th time delay less said fixed increment, where m is an integer.

4. The method set forth in claim 2 wherein step (c) comprises presenting said at least one subsequent stimulation pulse to the heart at the end of a second time delay after the occurrence of a detectable and repeatable cardiac event within a subsequent cardiac cycle, such as an R-wave, said second time delay comprising said first time delay plus a fixed increment, and wherein said prescribed scan pattern defines an mth time delay after which an mth simulation pulse is provided as being equal to an (m−1)th time delay plus said fixed increment, where m is an integer.

5. The method set forth in claim 2 wherein step (c) comprises presenting said at least one subsequent stimulation pulse to the heart at the end of a second time delay after the occurrence of a detectable and repeatable cardiac event, such as an R-wave, within a subsequent cardiac cycle, said second time delay comprising two fixed increments less than said first time delay, and wherein said prescribed scan pattern defines a third time delay as comprising one fixed increment greater than said second time delay, a fourth time delay as comprising two fixed increments less than said third time delay, a fifth time delay as comprising one fixed increment greater than said fourth time delay, and so on.

6. The method set forth in claim 1 wherein the location within the scan pattern where the at least one new stimulation pulse is provided upon the occurrence of a subsequent arrhythmia is backed up n steps, where n is an integer, from the location in the scan pattern that successfully terminated the first arrhythmia.

7. The method set forth in claim 6 wherein the number n comprises an integer within the range of one to fifteen.

8. The method set forth in claim 1 further including defining said prescribed scan pattern as a sequence of discrete times within a region of time of said cardiac cycle where successive stimulation pulses are to be respectively applied, and identifying each of said discrete times by an integer m, and further wherein step (e) comprises storing the value of m corresponding to the at least one stimulation pulse that successfully terminates the cardiac arrhythmia.

9. A method of terminating a cardiac arrhythmia comprising:
(a) monitoring a heart to determine the presence of a cardiac arrhythmia;
(b) generating a first sequence of stimulation pulses in response to a detected cardiac arrhythmia, said first sequence of stimulation pulses comprising a stimulation bundle that is applied to the heart during each cardiac cycle at a precise incremental time within the cardiac cycle that varies from cardiac cycle to cardiac cycle by a prescribed number of step increments, said stimulation bundle comprising at least one stimulation pulse;
(c) terminating the generation of said first sequence of stimulation pulses in response to the detected termination of said cardiac arrhythmia;
(d) generating a second sequence of stimulation pulses in response to the next detected cardiac arrhythmia, said second sequence of stimulation pulses being the same as said first sequence of stimulation pulses but commencing at a point within a cardiac cycle that is backed up a prescribed number of step increments from the location of the first sequence of stimulation pulses within the cardiac cycle when terminated in step (c).

10. The method of terminating a cardiac arrhythmia as set forth in claim 9 wherein step (b) comprises generating said first sequence of stimulation pulses in accordance with a scan pattern that causes a prescribed number of stimulation bundles to be applied to the heart, one stimulation bundle being applied during each cardiac cycle, with each successive stimulation bundle being applied to the heart at a time within the cardiac cycle that is less than the time of application of the most immediate prior stimulation bundle in said sequence, the time of application being determined relative to a detectable and repeatable event within the cardiac cycle, such as the occurrence of an R-wave; and further wherein step (d) comprises generating said second sequence of stimulation pulses to be a continuation of said first sequence of stimulation pulses commencing at a point in the first sequence of stimulation pulses that is baced up a prescribed amount from the point where the first sequence of stimulation pulses was terminated in step (c).

11. The method of terminating a cardiac arrhythmia as set forth in claim 10 wherein step (d) further includes backing up the starting point of the second sequence of stimulation pulses to a point in the first sequence that occurred n cardiac cycles prior to the termination of the first sequence in step (c), where n is an integer greater than one.

12. The method of terminating a cardiac arrhythmia as set forth in claim 11 wherein step (d) further includes storing identifying indicia, such as a bundle number or time of application, of the stimulation bundle generated immediately prior to the termination of the first sequence in step (c), and using this stored indicia to help define the starting point of the second sequence of stimulation pulses.

13. The method of terminating a cardiac arrhythmia as set forth in claim 9 wherein step (b) comprises generating said first sequence of stimulation pulses in accordance with a scan pattern that causes a prescribed number of stimulation bundles to be applied to the heart, one stimulation bundle during each cardiac cycle, with each successive stimulation bundle being applied to the heart at a time within the cardiac cycle that is greater than the time of application of the most immediate prior stimulation bundle in said sequence, the time of application being determined relative to a detectable and repeatable event within the cardiac cycle, such as the occurrence of an R-wave; and further wherein step (d) comprises generating said second sequence of stimulation pulses to be a continuation of said first sequence of stimulation pulses commencing at a point in the first sequence of stimulation pulses that is backed up a prescribed amount from the point where the first sequence of stimulation pulses was terminated in step (c).

14. The method of terminating a cardiac arrhythmia as set forth in claim 13 wherein step (d) further includes backing up the starting point of the second sequence of stimulation pulses to a point in the first sequence that occurred n cardiac cycles prior to the termination of the first sequence in step (c), where n is an integer greater than one.

15. The method of terminating a cardiac arrhythmia as set forth in claim 14 wherein step (d) further includes storing identifying indicia, such as a bundle number or time of application, of the stimulation bundle generated immediately prior to the termination of the first sequence in step (c), and using this stored indicia to help define the starting point of the second sequence of stimulation pulses.

16. A pacemaker for terminating a cardiac arrhythmia comprising:

means for detecting and confirming the occurrence of a cardiac arrhythmia;

means responsive to said confirming means for generating a heart-stimulating pulse at the end of a time delay following the last heartbeat within a time range which potentially allows the arrhythmia to be terminated;

means for incrementally scanning said time delay in discrete time intervals during successive cycles of operation of said pulse generating means;

means for detecting the termination of said cardiac arrhythmia;

means for ceasing the operation of said pulse generating means following termination of said cardiac arrhythmia;

means for registering the last-used time delay which was successful in terminating the cardiac arrhythmia; and means for adjusting said last-used time delay by a prescribed incremental amount and using said adjusted last-used time delay for first use in the next scan which follows cardiac arrhythmia confirmation.

17. The pacemaker as set forth in claim 16 wherein said scanning means includes means for scanning said time delay in accordance with a prescribed scan pattern.

18. The pacemaker as set forth in claim 17 further including externally controlled means for selectively programming said prescribed scan pattern to a desired scan pattern.

19. The pacemaker as set forth in the claim 18 wherein said prescribed scan pattern comprises a sequence of decreasing time delays.

20. The pacemaker as set forth in claim 18 wherein said prescribed scan pattern comprises a sequence of increasing time delays.

21. The pacemaker as set forth in claim 18 wherein said prescribed scan pattern comprises a first time delay, a second time delay that is less than said first time delay by two prescribed time increments, a third time delay that is greater than said second time delay by one prescribed time increment, a fourth time delay that is less than said third time delay by said two prescribed time increments, and so on, with an nth time delay being less than an (n−1)th time delay by said two prescribed time increments, and an (n+1)th time delay being greater than the nth time delay by said one prescribed time increment, where n is an integer.

22. The pacemaker as set forth in claim 21 further including externally controlled means for selectively adjusting said prescribed time increments.

23. The pacemaker as set forth in claim 16 further including externally controlled means for selectively adjusting the time range over which said time delay is scanned.

24. The pacemaker as set forth in claim 16 wherein said pulse generating means includes means for varying the energy of the heart stimulating pulse.

25. The pacemaker as set forth in claim 24 further including externally controlled means for selectively programming the energy of said heart stimulating pulse.

26. An implantable medical device for terminating a cardiac arrhythmia of a patient's heart comprising:

means for detecting a cardiac arrhythmia, said cardiac arrhythmia having a cardiac cycle associated therewith, said cardiac cycle including a narrow region of susceptibility therein during which a stimulation pulse applied to the heart has a high probability of terminating the cardiac arrhythmia;

means responsive to the detection of a cardiac arrhythmia by said detecting means for stimulating the heart with at least one stimulation pulse during said narrow region of susceptibility, said means including incremental scanning means for delivering a stimulation pulse to the heart during each cardiac cycle at a discrete time during the cardiac cycle that is defined by a prescribed scan pattern, said prescribed scan pattern presenting each successive stimulation pulse to the heart at a slightly different discrete time increment than was a prior stimulation pulse, thereby assuring that the narrow region of susceptibility is eventually located;

means for storing the location within said prescribed scan pattern of a stimulation pulse that successfully terminates said cardiac arrhythmia; and mean responsive to the detection of a subsequent arrhythmia by said detecting means for stimulating the heart with said scanning means beginning at a point in said prescribed scan pattern that is backed up from the location of the prior successful stimulation pulse in said prescribed scan pattern by a prescribed incremental amount;

whereby the initial stimulation pulse provided by said scanning means subsequent to the first occurrence of a cardiac arrhythmia commences at a location within the cardiac cycle that is near and moving towards, in accordance with the prescribed scan pattern, the location of the narrow region of susceptibility;

whereby, for cardiac arrhythmias occurring subsequent to the initial cardiac arrhythmia, the narrow region of susceptibility is located quickly by a stimulation pulse;

whereby cardiac arrhythmias occurring subsequent to the initial cardiac arrhythmia may be terminated quickly.

27. The implantable medical device of claim 26 wherein said prescribed scan pattern defines a scanning window of time within the cardiac cycle; said scanning window beginning at a prescribed time delay after a detectable cardiac event in each cardiac cycle,, such as the occurrence of an R-wave, and continuing for a sufficient time delay thereafter to likely cover the narrow region of susceptibility; said prescribed scan pattern defining discrete locations, or time delays, within the scanning window where a stimulation pulse is applied during a given cardiac cycle, a first stimulation pulse of the scan pattern being applied at a first location within the scanning window during a first cardiac cycle, a second stimulation pulse of the scan pattern being applied at a second location within the scanning window during a second cardiac cycle, and so on, with an nth stimulation pulse of the scan pattern being applied at an nth location within the scanning window during an nth cardiac cycle.

28. The implantable medical device of claim 27 wherein each stimulation pulse applied to the heart during each cardiac cycle has a location within the scanning window of that cardiac cycle that is successively increasing relative to a leading edge of said scanning window.

29. The implantable medical device of claim 27 wherein each stimulation pulse applied to the heart during each cardiac cycle has a location within the scanning window of that cardiac cycle that is successively decreasing relative to a leading edge of said scanning window.

30. The implantable medical device of claim 27 further including external control means that may be momentarily coupled to said implantable medical device for programmably adjusting said scan pattern and the prescribed time delay of said scanning window.

31. The implantable medical device of claim 30 further including means for increasing the energy of said stimulation pulse in the event none of the stimulation pulses defined by said scan pattern are effective in terminating said cardiac arrhythmia during a first pass through said scan pattern.

32. The implantable medical device of claim 26 further including pacemaker means for providing stimulation pulses on demand to the heart in order to maintain a desired heart rhythm.

* * * * *